United States Patent [19]

Chou

[11] Patent Number: 4,624,937

[45] Date of Patent: Nov. 25, 1986

[54] PROCESS FOR REMOVING SURFACE OXIDES FROM ACTIVATED CARBON CATALYST

[75] Inventor: Shine K. Chou, Chesterfield, Mo.

[73] Assignee: Monsanto Company, St. Louis, Mo.

[21] Appl. No.: 705,391

[22] Filed: Feb. 28, 1985

Related U.S. Application Data

[63] Continuation-in-part of Ser. No. 608,831, May 10, 1984, abandoned.

[51] Int. Cl.$^4$ .................. C01B 31/10; B01J 21/18; C07F 9/02; C07C 85/11
[52] U.S. Cl. .................. 502/180; 260/502.5 R; 423/460; 564/384; 564/394; 564/462; 564/468
[58] Field of Search ............... 502/180, 416, 423, 426, 502/434, 435; 423/460, 461

[56] References Cited

U.S. PATENT DOCUMENTS

| | | | |
|---|---|---|---|
| 1,810,871 | 6/1931 | Davis et al. | 502/435 |
| 3,243,383 | 3/1966 | Schultz et al. | 252/411 |
| 3,336,148 | 8/1967 | Gunnell et al. | 423/460 |
| 3,497,564 | 2/1970 | Allen et al. | 264/650 |
| 3,909,449 | 9/1975 | Nagai et al. | 502/434 |
| 3,969,398 | 7/1976 | Hershman | 260/502.5 |
| 4,055,628 | 10/1977 | McCarroll et al. | 423/460 |
| 4,072,706 | 2/1978 | Hershman et al. | 564/468 |
| 4,075,157 | 2/1978 | Johnson | 423/460 |
| 4,083,801 | 4/1978 | Das | 502/426 |
| 4,139,416 | 2/1979 | Palumbo | 423/460 |
| 4,158,643 | 6/1979 | Simha | 423/247 |
| 4,264,776 | 4/1981 | Hershman et al. | 564/384 |

FOREIGN PATENT DOCUMENTS

| | | | |
|---|---|---|---|
| 52-72393 | 6/1977 | Japan | 423/460 |
| 53-3991 | 1/1978 | Japan | 423/461 |
| 56-17634 | 2/1981 | Japan | 502/180 |
| 0567666 | 9/1977 | U.S.S.R. | 502/426 |

OTHER PUBLICATIONS

*Active Carbon–Manufacture–Properties Applications*–Smisek & Cerny, Elsever Publishing Co., N.Y., N.Y.–1970–p. 66.

Primary Examiner—P. E. Konopka
Attorney, Agent, or Firm—Frank D. Shearin

[57] ABSTRACT

An improved process is provided for the selective production of secondary amines and primary amines by bringing together under reaction conditions a tertiary amine or a secondary amine with oxygen or an oxygen-containing gas in the presence of an activated carbon catalyst, the improvement which comprises using an activated carbon catalyst wherein oxides have been removed from the surface of the carbon.

3 Claims, No Drawings

PROCESS FOR REMOVING SURFACE OXIDES FROM ACTIVATED CARBON CATALYST

CROSS REFERENCE TO RELATED APPLICATION

This application is a continuation-in-part of Application Ser. No. 608,831 filed May 10, 1984 and now abandoned.

BACKGROUND OF THE INVENTION

The present invention relates to an improved oxidation catalyst and, more particularly, to a method for enhancing the catalytic activity of activated carbon for use in oxidation reactions.

U.S. Pat. No. 4,264,776 discloses and claims a process for preparing secondary amines by catalytic oxidation of tertiary amines with oxygen over carbon catalyst. The catalyst is an activated carbon of the type well known in the art and characterized by high absorptive capacity for gases, vapors, and colloidal solids and relatively high specific surface areas. Activation of commercially available carbon catalysts is usually achieved by heating the carbon to high temperatures (800° C. to 900° C.) with steam or with carbon dioxide which brings about a porous particulate structure and increased specific surface area.

U.S. Pat. No. 4,072,706 discloses a process for oxidative removal of phosphonomethyl groups from tertiary amines in which a molecular oxygen-containing gas is employed along with an activated carbon catalyst. It is noted that any source or form of carbon can be used as a catalyst or substrate in the process of the disclosed invention.

U.S. Pat. No. 3,969,398 teaches the use of activated carbon in the catalytic oxidation of N-(phosphonomethylimino)diacetic acid. It is stated that the carbon catalysts useful in the claimed process are available under a large number of trade names.

U.S. Pat. No. 3,497,564 discloses the use of amorphous or graphitic carbon as a catalyst in the oxidative dehydrogenation of alkylbenzenes. It is taught that activated carbon of whatever origin is operable in the process.

Japanese Patent Application 56-17634 discloses an activation method for $SO_3/SO_2$ conversion carbon materials which are useful as reduction catalysts to convert selectively $SO_3$ in various gases, such as air and exhaust, to $SO_2$. Carbon materials, such as cylindrical activated carbon, are treated with an oxidizing acid, e.g., nitric acid, followed by heat treatment at 300° C. to 700° C. under an inert gas.

U.S. Pat. No. 4,158,643 teaches a method for oxidative modification of an activated carbon support in which oxygen is added to the surface of the activated carbon, and then the carbon support is impregnated with an inert hydrophobic compound. The carbon support, which may be any commercially available activated carbon for vapor phase activation use, is useful in oxidizing carbon monoxide in the presence of sulfur dioxide for an extended period of time.

U.S. Pat. No. 3,243,383 teaches a method for regenerating spent catalysts which have been used for polymerizing olefins to liquid products. According to the disclosure, spent cobalt oxide on carbon catalyst is heated in an inert atmosphere, cooled, and then treated with nitric acid, nitric oxide, or nitrogen dioxide.

None of the foregoing references suggests that the surface of a carbon catalyst, particularly where acidic and basic surface oxides can be present, can play an important role in amine oxidation rates.

SUMMARY OF THE PRESENT INVENTION

The present invention provides a method for preparing activated carbon for catalytically oxidizing tertiary amines or secondary amines in the presence of oxygen or an oxygen-containing gas to selectively produce secondary or primary amines which comprises the step of treating the carbon catalyst to remove oxides from the surface thereof. To accomplish the removal of surface oxides, a treatment sequence is followed which comprises subjecting the carbon material to an oxidizing agent, such as nitric acid, $CrO_3$, $H_2O_2$, hypochlorite and the like, or an oxidant gas, such as $H_2O$, $H_2O/NH_3$, $CO_2$, $NO_x$, air, etc. and then pyrolyzing it in an oxygen-free atmosphere at a temperature in the range of about 500° C. to 1500° C.

However, the treatment can also be accomplished by simultaneously pyrolyzing the carbon material in the presence of $NH_3$ and an oxygen-containing gas that will react with the oxides on the surface of the carbon at pyrolyzing temperatures. Suitable oxygen-containing gases include steam, $NO_x$, $O_2$, $CO_2$, $SO_2$ and mixtures of such gases.

Thus, it can be seen that in another embodiment of this invention there is provided an improved process for the selective production of secondary amines and primary amines by bringing together under reaction conditions a tertiary amine or a secondary amine with oxygen or an oxygen-containing gas in the presence of an activated carbon catalyst, the improvement which comprises using an activated carbon catalyst wherein oxides have been removed from the surface thereof.

As used herein the term "oxides" is intended to mean carbon functional groups which contain oxygen as well as hetero atom functional groups which contain oxygen. Other hetero atom functional groups which do not contain oxygen may also be removed from the surface of the carbon material during treatment.

Activated carbons prepared according to the process of this invention demonstrate unexpectedly improved activity, i.e., reaction rates, in the catalytic oxidation of tertiary amines to selectively produce secondary amines. Moreover, the oxidative removal of carboxymethyl and phosphonomethyl groups from tertiary amines and secondary amines and the catalytic oxidation of N-(phosphonomethylimino)diacetic acid can be significantly enhanced using a carbon catalyst treated according to this invention, without regard to the kind of carbon material employed.

DETAILED DESCRIPTION OF THE INVENTION

According to the present invention, the activity of carbon as a catalyst in the oxidation of tertiary amines to secondary amines and in the oxidation of secondary amines to primary amines can be greatly enhanced if the carbon material is first subjected to a treatment process to remove surface oxides. In carbon catalyzed oxidation reactions, an analysis of the catalysis mechanism tends to suggest a possible correlation between catalyst activity and surface area and/or pore size distribution. It has now been discovered that the presence of basic and acidic oxides on the surface of the carbon material can play a significant role in the oxidation process. Although applicant does not wish to be bound by any particular theory, it is believed that the catalytic activity of the catalyst can be substantially increased if the acidic oxides are removed from the surface of the carbon.

U.S. Pat. No. 4,264,776, the teachings of which are incorporated herein by reference, describes a wide variety of carbon materials which can be used in practicing this invention. Ordinarily the carbon catalyst is a commercially available activated carbon with a carbon content ranging from about 10% for bone charcoal to about 98% for some wood chars and nearly 100% for activated carbons derived from organic polymers. The noncarbonaceous matter in commercially available carbon materials will normally vary depending on such factors as precursor origin, processing, and activation method. For example, inorganic "ash" components containing aluminum and silicon can be present in large amounts accompanied by certain alkali metals and alkaline earths. The latter grouping influences the acidity-basicity characteristics of the activated carbon. Among other inorganic elements often found in activated carbons are iron and titanium. Depending on raw material origin and activation procedure, large amounts of oxygen can be present along with lesser amounts of hydrogen, nitrogen, sulfur, and other organic functional groups. Despite the wide variety of elements and impurities which can comprise an individual commercially available carbon material, the process of this invention is applicable to all commercially available activated carbon catalyst materials.

Following is a listing of some of the activated carbons which have demonstrated enhanced activity after treatment according to this invention. The list is presented for illustration and should not be interpreted as limiting the applicability of this invention. Preferably, the carbons are in the form of powders, although granules or any other suitable particulate form or shape can be employed in practicing this invention.

| Trade Name | Sold By |
|---|---|
| Darco G-60 Spec | ICI-America Wilmington, Delaware |
| Darco X | ICI-America Wilmington, Delaware |
| Norit SG Extra | Amer. Norit Co., Inc. Jacksonville, Florida |
| Norit EN4 | Amer. Norit Co., Inc. Jacksonville, Florida |
| Norit EXW | Amer. Norit Co., Inc. Jacksonville, Florida |
| Norit A | Amer. Norit Co., Inc. Jacksonville, Florida |
| Norit Ultra-C | Amer. Norit Co., Inc. Jacksonville, Florida |
| Norit ACX | Amer. Norit Co., Inc. Jacksonville, Florida |
| XZ | Barnebey-Cheney Columbus, Ohio |
| NW | Barnebey-Cheney Columbus, Ohio |
| JV | Barnebey-Cheney Columbus, Ohio |
| BL Pulv. | Pittsburgh Activated Carbon Div. of Calgon Corporation Pittsburgh, Pennsylvania |
| PWA Pulv. | Pittsburgh Activated Carbon Div. of Calgon Corporation Pittsburgh, Pennsylvania |
| PCB Fines | Pittsburgh Activated Carbon Div. of Calgon Corporation Pittsburgh, Pennsylvania |
| P-100 | No. Amer. Carbon, Inc. Columbus, Ohio |
| Nuchar CN | Westvaco Corporation Carbon Department Covington, Virginia |
| Nucher C-1000 N | Westvaco Corporation Carbon Department Covington, Virginia |
| Nuchar C-190 A | Westvaco Corporation Carbon Department Covington, Virginia |
| Nuchar C-115 A | Westvaco Corporation Carbon Department Covington, Virginia |
| Code 1551 | Baker and Adamson Division of Allied Amer. Norit Co., Inc. Jacksonville, Florida |
| Norit 4 × 14 mesh | Amer. Norit Co., Inc. Jacksonville, Florida |
| Gl-9615 | Barnebey-Cheney Columbus, Ohio |
| VG-8408 | Barnebey-Cheney Columbus, Ohio |
| VG-8590 | Barnebey-Cheney Columbus, Ohio |
| NB-9377 | Barnebey-Cheney Columbus, Ohio |
| Grade 235 | Witco Chemical Corp. Activated Carbon Div. New York, New York |
| Grade 337 | Witco Chemical Corp. Activated Carbon Div. New York, New York |
| Grade 517 | Witco Chemical Corp Activated Carbon Div. New York, New York |
| Grade 256 | Witco Chemical Corp. Activated Carbon Div. New York, New York |
| Columbia SXAC | Union Carbide New York, New York |

In practicing this invention, the treatment process can be accomplished by a single or a multistep scheme which in either case results in an overall chemical reduction of oxides on the carbon surface, i.e., a reduction or removal of acidic oxides from the carbon surface.

In a two-step scheme, the carbon material can be first treated with an oxidizing agent such as, for example, liquid nitric acid, nitrogen dioxide, $CrO_3$, air, oxygen, $H_2O_2$, hypochlorite, or a mixture of gases obtained by vaporizing nitric acid. The treatment can be accomplished using either a gas or a liquid oxidizing agent. Where a liquid is used, concentrated nitric acid containing from about 10 to about 80 gm $HNO_3$ per 100 gm of aqueous solution is preferred. Preferred gaseous oxidants include oxygen, nitrogen dioxide, and nitric acid vapors. A particularly effective oxidant is nitric acid in the vapor phase which includes nitric acid carried into the vapor phase by an entraining gas as well as the vapors obtained by distilling liquid nitric acid. With a liquid oxidant, temperatures from about 60° C. to about 90° C. are appropriate, but with gaseous oxidants, it is often advantageous to use temperatures of about 50° C. to about 500° C. or even higher for the treatment step.

The treatment can be achieved by placing carbon from a manufacturer in a round bottom flask which contains a magnetic stirring bar. Liquid nitric acid is selected as the oxidizing agent for illustration. The amount of carbon used is determined by the percent carbon load desired (% carbon load=gm of carbon used per 100 ml of nitric acid solution) and the nitric acid solution volume to be used. Ordinarily, 1 to 200 gm of carbon per 100 ml of nitric acid or other liquid oxidizing agent is satisfactory. Temperature control can be provided by any suitable means. A condenser and scrubber can be connected to the round bottom of the flask as desired. A calculated volume of water, preferably deionized water, is added to the carbon, followed by sufficient 69-71% nitric acid to achieve the desired nitric acid solution. The carbon and nitric acid solution are then stirred for the desired period at the desired temperature. Experimental results indicate that carbon load, temperature, nitric acid concentration, etc. in the first treatment step are not particularly critical to achieving the desired oxidation of the carbon material and thus may be governed by convenience over a wide range. The highest possible carbon load is preferred for economic reasons.

After stirring the carbon is filtered, and the resulting wet cake may or may not be washed and/or dried prior to pyrolysis.

The time during which the carbon is treated with the oxidant can vary widely from about 5 minutes to about 10 hours. Preferably, a reaction time of about 30 minutes to about 6 hours is satisfactory. When concentrated nitric acid is the oxidant, a contact time of about 30 minutes to about 3 hours is satisfactory.

In a second step, the oxidized carbon material is pyrolyzed, i.e., heat treated, at a temperature in the range of about 500° C. to about 1500° C., preferably from about 800° C. to 1200° C. In one embodiment of this invention, the pyrolysis is conducted in an atmosphere such as nitrogen containing small amounts of steam or carbon dioxide, which is believed to aid in the pyrolysis. As will occur to those skilled in the art in view of this disclosure, the oxides will be removed from the surface of the carbon at pyrolysis temperatures, but the presence of oxygen-containing gases such as steam or carbon dioxide should be avoided as the carbon cools below pyrolysis temperatures to avoid the re-formation of surface oxides. Accordingly, it is preferred to conduct the pyrolysis in an inert gas atmosphere, such as nitrogen, argon or helium.

Wet cake or dry carbon is placed in a ceramic pyrolysis dish which together are placed in a quartz tube. In one embodiment of this invention, nitrogen gas is passed through water at about 70° C., then through the quartz tube during pyrolysis. In an alternate embodiment, a dry, static nitrogen atmosphere is maintained after flushing the quartz tube with several tube volumes of dry nitrogen prior to pyrolysis. The quartz tube containing the pyrolysis dish is placed in a suitable pyrolyzer apparatus at about 930° C. for the desired period, followed by cooling while maintaining the nitrogen atmosphere.

Pyrolysis can last anywhere from about 5 minutes to 60 hours, although 10 minutes to 6 hours is normally satisfactory. The shorter times are preferred for economic reasons because, as might be expected, continued exposure of the carbon to elevated temperatures for prolonged periods can result in a poor carbon catalyst for the oxidation. In addition, although applicant does not wish to be bound by any particular theory, it is believed that prolonged heating at pyrolysis temperatures favors the formation of graphite, and it is believed that graphite is not as satisfactory as activated carbon for the oxidative conversion of tertiary and secondary amines to secondary and primary amines. It is preferred that the pyrolysis occurs in a slightly moist atmosphere or an atmosphere which contains $NH_3$ as this appears to produce a more active catalyst in a shorter time.

In a preferred embodiment of this invention, the treatment is accomplished in a single step by pyrolyzing the carbon material as described above while simultaneously passing a gas stream comprised of $NH_3$ and an oxygen-containing gas e.g., $H_2O/NH_3$, through the carbon. Although it is not a critical feature of this invention, the flow rate of the gas stream should be fast enough to achieve adequate contact between fresh gas reactants and the carbon surface, yet slow enough to prevent excess carbon weight loss and material waste. Many $NH_3$/oxygen-containing gas mixtures can be used such as, for example, $NH_3/CO_2$, $NH_3/O_2$, $NH_3/H_2O$ and $NH_3/NO_x$, provided the gas mixture achieves the desired result. Ordinarily, the oxygen-containing gas/$NH_3$ ratio can range from 0:100 to 90:10. Furthermore, nitrogen can be used as a diluent to prevent severe weight loss of the carbon in high oxygen-containing gas concentrations. Ammonia is a basic gas, and, as such, is believed to assist the decomposition of the various oxide groups on the surface of the carbon material. Any other chemical entity which will generate $NH_3$ during pyrolysis should also prove satisfactory as an $NH_3$ source. For economic reasons an $NH_3/H_2O$ gas stream is most preferred in practicing the process of this invention.

The carbon materials treated according to the process of this invention, when used in the catalytic oxidation of tertiary amines and secondary amines, demonstrate substantially increased activity, i.e., faster reaction rates, than commercially available activated carbons. Reaction rates, for example, can be increased up to 30 times and higher the rate obtainable with otherwise untreated commercial activated carbon catalysts, all other oxidation reaction conditions remaining unchanged. Surprisingly, even carbons which are initially inactive, such as carbon black and sugar charcoal, for example, can be activated according to the process of this invention. In addition to the catalytic oxidation of tertiary and secondary amines, carbon catalysts prepared according to this invention improve the oxidative removal of carboxymethyl groups and phosphonomethyl groups from tertiary amines as well as the catalytic oxidation of N-(phosphonomethylimino)diacetic acid.

The present invention can be more clearly illustrated by the following examples.

EXAMPLE 1

This example illustrates the improved results that are obtained by the catalysts of this invention when used to convert a tertiary amine to a secondary amine.

Twenty-two powdered activated carbon samples were obtained from commercial sources, and a portion of each was subjected to the two-step treatment process described above. Approximately 12 grams of the carbon were placed in a 250 milliliter round-bottomed flask equipped with a magnetic stirrer. Then, 100 milliliters of 18.1 percent nitric acid was added to the flask, and the contents were heated to about 85° C. to about 100° C. for six hours. The flask was allowed to cool to room temperature and the carbon was separated from the acid solution by filtration on a porous frit. The carbon was dried overnight in an oven at 85° C., then placed in a ceramic pyrolysis dish. The dish and the carbon were placed in a quartz tube. Dry nitrogen was passed through the tube while heating the tube and contents to approximately 930° C. Heating was continued for one hour. The heating was discontinued and the tube and contents were allowed to cool to room temperature while maintaining the flow of nitrogen over the carbon during cooling.

A portion of the treated and untreated carbon from each sample was then used as a catalyst in the oxidation of 7.3 gm N-(phosphonomethylimino)diacetic acid in 92 ml of water to produce N-phosphonomethylglycine. The catalyst charge was 1.2 gm for each run. Data obtained from observing each reaction are shown below in Table I. The amine oxidation was performed in an autoclave made by Autoclave Engineers at 85° C. and 50–55 psig oxygen pressure using an oxygen flow rate through the autoclave of 200 ml/min.

TABLE I

| | Amine Oxidation Time (Minutes) | |
|---|---|---|
| Carbon Type | Treated Catalyst | Untreated Catalyst |
| Calgon C | 20 | 40 |
| Calgon BL | 17 | 38 |
| Calgon RC | 11 | 50 |
| Darco GFP | 15 | 36 |
| Darco FM-1 | 10 | 66 |
| Darco TRS | 13 | 58 |
| Darco S51 | 18 | 80 |
| Darco S-51FF | 10 | 55 |
| Darco S-51K | 13 | 113 |
| Darco BG | 13 | 40 |
| Darco KB | 14 | 136 |
| Darco FM-1 | 11 | 66 |
| Norit W20 | 16 | 69 |
| Norit F | 15 | 61 |
| Norit FQA | 23 | >100 |
| Norit SA4 | 11 | 39 |
| Norit PN3 | 11 | 36 |
| Norit A | 8 | 46 |
| Nuchar Aqua Pac | 18 | 75 |
| Nuchar Aqua S | 10 | 57 |
| Nuchar Experimental "A" | 12 | 29 |
| Nuchar Experimental "B" | 12 | 29 |

EXAMPLE 2

Six portions of Norit W20 carbon were subjected to the two-step treatment of example 1 except that the pyrolysis time was varied from one to six hours. Results are shown in Table 2.

TABLE 2

| | Amine Oxidation Time (Minutes) | |
|---|---|---|
| Pyrolysis time (hours) | Treated Catalyst | Untreated Catalyst |
| 1 | 16 | 69 |
| 2 | 11 | — |
| 3 | 11 | — |
| 4 | 11 | — |
| 5 | 6 | — |
| 6 | 10 | — |

EXAMPLE 3

In a 1.9 cm I.D. $\times$ 40.6 cm length quartz tube is placed 2.5 gm of Calgon C 450 activated carbon. The tube is connected to a gas stream resulting from sparging a 70 to 100 ml/min. $N_2$ stream through a 70° C., 10% $NH_4OH$ aqueous solution. The quartz tube is then placed in a preheated 30.5 cm tubular furnace and pyrolyzed at 930° C. for 60 min. and cooled to room temperature under a dry $N_2$ atmosphere without contacting any air.

The above carbon is used to oxidize various tertiary amines to secondary amines in a 300 ml autoclave made by "Autoclave Engineering" at 85° C., $3.44 \times 10^5$ N/m$^2$ pressure and 200 ml/min. $O_2$ flow rate. The samples are analyzed by HPLC. The concentration of the reactant, catalyst load, and reaction times of treated catalyst vs. untreated catalyst of various tertiary amines are listed in Table 3 along with the reaction end point which can be determined by any one of several convenient methods known to those skilled in the art.

TABLE 3

| | | Amine Oxidation Time (Minutes) | | |
|---|---|---|---|---|
| Reactant | Reactor-Load | Untreated Catalyst | Treated Catalyst | Desired Product |
| Nitrilotriacetic acid | 4 gm Reactant 96 ml H$_2$O 0.2 gm Catalyst | >100 | 19.5 | Iminodiacetic acid |
| N—phosphonomethyl-N—(n-propyl)glycine | 2.0 gm Reactant 98 ml H$_2$O 0.1 gm Catalyst | >60 | 10 | N—n-propyl-aminomethyl-phosphonic acid |
| N—phosphonomethylimino-diacetic acid | 7.5 gm Reactant 92 ml H$_2$O 0.2 gm Catalyst | >400 | 33 | N—phosphono-methylglycine |
| Trisphosphonomethylamine N(CH$_2$PO$_3$H$_2$)$_3$ | 5 gm Reactant 95 ml H$_2$O 0.2 gm Catalyst | >100 | 61.5 | Bisphosphono-methylamine |

EXAMPLE 4

In a 1.9 cm I.D. $\times$ 35.6 cm long quartz tube was placed 3.55 gm of Norit W-20 activated carbon. The tube was connected to streams of 50 ml/min. of NH$_3$ gas and 89 ml/min. of steam and then placed in a preheated 30.5 cm tubular furnace and pyrolyzed at 930° C. for 30 minutes. The tube was then cooled to room temperature under a dry N$_2$ atmosphere without any contact with air. The resulting carbon gave 54% weight loss.

Then, 7.3 gm of N-(phosphonomethylimino)diacetic acid, 1.2 gm of the above catalyst and 92 ml of H$_2$O were mixed in a 300 ml autoclave made by "Autoclave Engineers" and oxidized at 70° C., $3.44 \times 10^5$ N/m$^2$ O$_2$ pressure and 200 ml/min. O$_2$ flow rate. The reaction finished at 9.7 min. The rate of reaction using the treated catalyst was 11.4 times faster than the reaction using the untreated catalyst.

What is claimed is:

1. A process for preparing an activated carbon catalyst for catalytically oxidizing tertiary amines and secondary amines in the presence of oxygen or an oxygen containing gas to selectively produce secondary amines and primary amines which comprises pyrolyzing activated carbon at a temperature in the range of about 800° C. to about 1200° C. while simultaneously passing over the activated carbon a gas stream comprised of an oxygen-containing gas and NH$_3$ wherein the oxygen-containing gas/NH$_3$ is in a ratio of up to 90:10 for a time sufficient to remove surface oxides from the carbon.

2. The process of claim 1 wherein the oxygen-containing gas is selected from the group consisting of H$_2$O, NO$_x$, O$_2$, CO$_2$, SO$_2$ and mixtures thereof.

3. The process of claim 1 wherein the oxygen-containing gas stream is NH$_3$/H$_2$O.

* * * * *